(12) United States Patent
Laurence et al.

(10) Patent No.: US 10,732,300 B2
(45) Date of Patent: Aug. 4, 2020

(54) ENERGY CALIBRATION WITH LU SPECTRUM SUBTRACTION

(71) Applicant: KONINKLIJKE PHILIPS N.V., Eindhoven (NL)

(72) Inventors: Thomas Leroy Laurence, North Royalton, OH (US); Sharon Xiaorong Wang, Highland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 113 days.

(21) Appl. No.: 15/768,029

(22) PCT Filed: Oct. 12, 2016

(86) PCT No.: PCT/EP2016/074499
§ 371 (c)(1),
(2) Date: Apr. 13, 2018

(87) PCT Pub. No.: WO2017/071958
PCT Pub. Date: May 4, 2017

(65) Prior Publication Data
US 2018/0341027 A1 Nov. 29, 2018

Related U.S. Application Data

(60) Provisional application No. 62/248,425, filed on Oct. 30, 2015.

(51) Int. Cl.
*G01T 1/163* (2006.01)
*G01T 1/29* (2006.01)
(Continued)

(52) U.S. Cl.
CPC ............ *G01T 1/163* (2013.01); *G01T 1/2985* (2013.01); *G01T 7/005* (2013.01); *G06F 19/00* (2013.01); *G16H 40/40* (2018.01)

(58) Field of Classification Search
CPC ....... G01T 1/163; G01T 7/005; G01T 1/2985; G06F 19/00; G16H 40/40
See application file for complete search history.

(56) References Cited

U.S. PATENT DOCUMENTS 7,633,057 B2 12/2009 Cooke
8,173,953 B2 5/2012 Stoller
9,500,753 B2 * 11/2016 Moake ..................... G01V 5/06

OTHER PUBLICATIONS

Song et al: "A sub-millimeter resolution PET detector module using a multi-pixel photon counter array; Sub-millimeter resolution PET detector module using a multi-pixel photon counter array", Physics in Medicine and Biology, Institute of Physics Publishing, Bristol GB, vol. 55, No. 9, May 7, 2010.

(Continued)

*Primary Examiner* — David P Porta
*Assistant Examiner* — Meenakshi S Sahu (57) ABSTRACT

The present application relates generally to positron emission tomography (PET). It finds particular application in conjunction with energy calibration of a digital PET (DPET) detector and will be described with particular reference thereto. In one aspect, a difference spectrum is produced by finding a difference between a background radiation spectrum with no radioactive source loaded and a calibration source radiation spectrum with a radioactive source loaded. The difference spectrum may then be used to identify an energy peak.

20 Claims, 5 Drawing Sheets

(51) Int. Cl.
*G01T 7/00* (2006.01)
*G16H 40/40* (2018.01)
*G06F 19/00* (2018.01)

(56) References Cited

OTHER PUBLICATIONS

Yao et al: "Lutetium oxyorthosilicate (LSO) intrinsic activity correction and minimal detectable target activity study for SPECT imaging with a LSO-based animal PET scanner; LSO intrinsic activity correction and MDTA study for SPECT imaging with a LSO-based animal PET scanner", Physics in Medicine and Biology, Institute of Physics Publishing, Bristol GB, vol. 53, No. 16, Aug. 21, 2008.

\* cited by examiner

ENERGY CALIBRATION WITH LU SPECTRUM SUBTRACTION

CROSS REFERENCE TO RELATED APPLICATIONS

This application is the U.S. National Phase application under 35 U.S.C. § 371 of International Application No. PCT/EP2016/074499, filed Oct. 12, 2016, published as WO 2017/071958 on May 4, 2017, which claims the benefit of U.S. Provisional Patent Application No. 62/248,425 filed Oct. 30, 2015. These applications are hereby incorporated by reference herein.

BACKGROUND

The following relates generally to nuclear imaging detector calibration for system such as positron emission tomography (PET) or single photon emission tomography (SPET). It finds particular application in conjunction with energy calibration of a digital PET (DPET) detector and will be described with particular reference thereto. However, it is to be understood that it also finds application in other usage scenarios and is not necessarily limited to the aforementioned application.

In nuclear medicine, radiation events may be detected by scintillators viewed by photodetectors. Using PET as an example, a 511 keV gamma ray characteristic of a positron-electron annihilation event is absorbed by a scintillator crystal which generates a flash (i.e. scintillation) of light. The photodetectors generate a count of photons (in the case of DPET, or a detector electric current in the case of photomultiplier detectors) and the summed photon count or electric current represents the energy of the detected 511 keV gamma ray. Raw mode data of the radiation events includes the position, energy, and timestamp of each detected radiation event. These raw data are first filtered by an energy window, e.g. 511 keV energy windowing for PET, followed by coincidence detection (for PET). Performing the energy windowing before the coincidence detection advantageously greatly reduces the number of events that must be correlated by the coincidence detection.

At a low level, particle energy is measured in terms of the summed photon count or current generated by the photodetector in response to a scintillation. At a higher level, the output is a particle energy value for a detected particle. However, because of individual variations amongst detectors and/or detector electronics, the energy value output by a given detector pixel may differ from the true particle energy by some amount. This variation is corrected by energy calibration. In a typical energy calibration approach, a radioactive calibration source emitting at the energy of interest (511 keV for PET) is loaded into the imaging system and raw data are collected for the calibration source. These raw data are sorted into an event count-versus energy histogram (event-energy histogram). Since the calibration source is designed to have a strong emission at 511 keV, the event-energy histogram should provide a large peak for 511 keV. Any deviation from this 511 keV energy is corrected by multiplying the energy by an energy correction factor. Because of detector non-linearity, this correction factor may be different for different particle energy ranges. One specification of PET detectors is energy resolution, which characterizes how well a detector rejects (e.g., filters) scatter events. The better the scatter rejection capability of a detector, the higher the contrast of the generated images. By way of illustration, energy resolution is an important parameter for DPET systems used to perform quantitative analysis of a treatment's effectiveness over time. A smaller energy resolution helps to keep scatter events away from the true activity distribution and, therefore, improves the accuracy of standardized uptake value (SUV). Calibration of DPET detectors is important to improving energy resolution.

The following provides a new and improved systems and methods which overcome the above-referenced problems and others.

SUMMARY

In accordance with one aspect, a device for performing energy calibration of a nuclear imaging instrument includes at least one electronic processor programmed to: construct a background radiation spectrum from event data acquired by the nuclear imaging instrument with no radioactive source loaded; construct a calibration source radiation spectrum from event data acquired by the nuclear imaging instrument with a radioactive source loaded that emits radiation particles with a known energy; calculate a difference spectrum as a difference between the calibration source radiation spectrum and the background radiation spectrum; identify a peak energy of a peak in the difference spectrum; and compute an energy correction factor that shifts the identified peak energy to the known energy. The at least one electronic processor may be further programmed to: multiply the calibration source radiation spectrum by the energy correction factor to produce a calibration source cluster event-energy spectrum; multiply the background radiation spectrum by the energy correction factor to produce a background cluster event-energy spectrum; calculate a cluster energy difference spectrum by subtracting the background cluster event-energy spectrum from the calibration source cluster event-energy spectrum; identify a cluster peak energy of a lower-energy peak in the cluster energy difference spectrum wherein the identified cluster peak energy is lower than the identified peak energy; and compute a cluster energy correction factor that shifts the identified cluster peak energy to a known cluster energy corresponding to the known energy.

In accordance with another aspect, a positron emission tomography (PET) imaging device includes: a PET imaging detector comprising scintillators optically coupled with photodetectors, the PET imaging detector comprising detector pixels. The PET imaging device may further include at least one electronic processor programmed to, for each detector pixel: construct a background radiation spectrum from event data acquired by the detector pixel with no radioactive source loaded; construct a calibration source radiation spectrum from event data acquired by the detector pixel with a radioactive source loaded that emits 511 keV radiation; calculate a difference spectrum as a difference between the calibration source radiation spectrum and the background radiation spectrum; identify a peak energy of a peak in the difference spectrum; and compute an energy correction factor that shifts the identified peak energy to 511 keV.

In accordance with yet another aspect, a nuclear imaging device includes: a nuclear imaging instrument comprising scintillators optically coupled with photodetectors to define an array of detector pixels. The nuclear imaging device may further include at least one electronic processor programmed to, for each detector pixel: construct a background radiation spectrum from event data acquired by the detector pixel with no radioactive source loaded; construct a calibration source radiation spectrum from event data acquired by the detector pixel with a radioactive source loaded that emits radiation at a known energy; calculate a difference spectrum as a difference between the calibration source radiation spectrum and the background radiation spectrum; identify a peak energy of a peak in the difference spectrum corresponding to the known energy; and compute an energy correction factor that shifts the identified peak energy to the known energy.

One advantage resides in improved nuclear imaging techniques.

Another advantage resides in improved computational and/or processing time for processor(s) in nuclear imaging equipment.

Another advantage resides in suppression of the impact on nuclear imaging of background radiation produced by scintillator devices.

Another advantage resides in more accurate nuclear imaging equipment.

Another advantage resides in a reduced calibration time in a calibration process of nuclear imaging equipment.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

DETAILED DESCRIPTION

As part of detector calibration, the detector signal corresponding to 511 keV (for PET; or other particle energy window) is determined. The radiation detector comprises an array of detector pixels, and this energy calibration is preferably performed on a per-pixel basis. In one design, there is a 1:1 correspondence between silicon photomultipliers (SiPM) detectors and scintillator crystals, and each such unit defines a detector pixel. In other embodiments other ratios may be employed. A given 511 keV particle may be detected by a single pixel (yielding the maximum energy, Emax), or may be detected by a contiguous cluster of 2, 3, or 4 pixels (in which case the sum of energies detected by the cluster should be about Emax).

One approach for energy calibration is to load and measure a radioactive calibration source and acquire data. Detectors may be calibrated to a 511 keV peak using a sealed source (e.g., Na-22 or Ge-68) or liquid (e.g., FDG). However, it is recognized herein that this approach can produce erroneous results due to background radioactivity of the scintillator crystal. In particular, lutetium (especially the radioisotope $^{176}$Lu) in LSO and LYSO scintillator crystals spontaneously decays to emit gamma radiation at 88 keV, 202 keV, and 307 keV. The latter two sum to 509 keV which is close to the 511 keV gamma rays emitted in electron positron annihilation events. More generally, the LSO or LYSO scintillator's natural background radiation exhibits peaks at these three energies along with a broad spectral structure extending from below 200 keV up to well above 511 keV. While scintillator crystals containing lutetium are described herein as illustrative examples, more generally scintillator crystals typically include one or more relatively heavy elements to provide high stopping power for radioactive particles, and many such heavy elements emit a significant degree of background radiation. This background radiation complicates determination of the 511 keV energy and reduces its accuracy. The problem is even greater for calibration of lower energies corresponding to cluster events detected by 2, 3, or 4 pixels.

In view of this, some methods described herein measure the calibration source and background radiation spectra (histograms of event counts versus energy, e.g. measured by digital detector signal), and subtract the latter from the former before performing the energy calibration.

Figure 1:
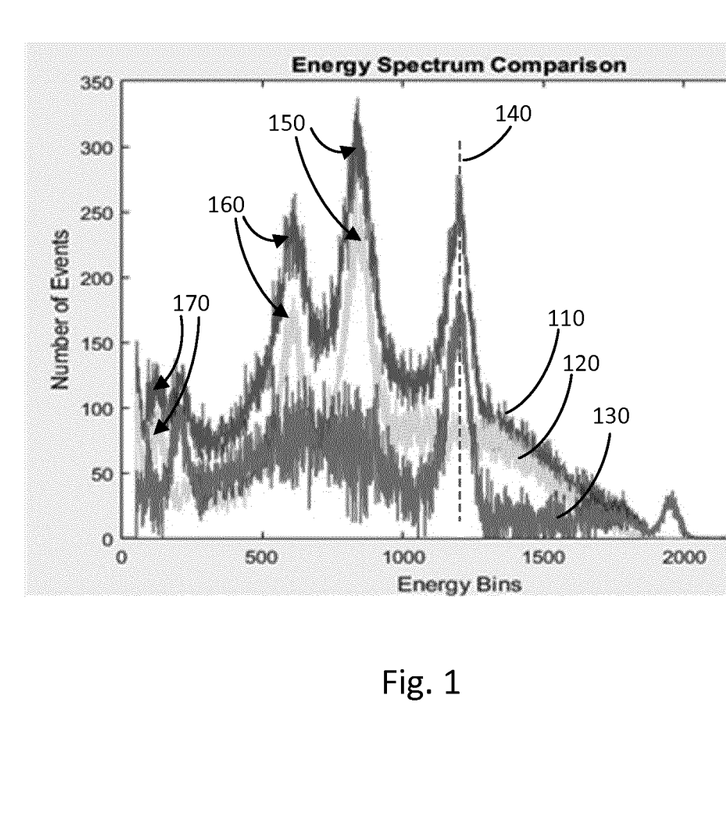
FIG. 1 illustrates an eMax (max single pixel) energy spectrum comparison.

FIG. 1 illustrates an eMax (max single pixel) energy spectrum comparison. In FIG. 1, curve 110 is the spectrum measured for a loaded Na22 calibration source. Ideally, this spectrum should show a strong 511 keV peak in relative isolation. However, a significant obscuring background signal is observed. This background is due (at least in substantial part) to background radiation emitted by the scintillator crystal itself, and more particularly the lutetium background. The 511 keV peak is riding on top of this lutetium background, which complicates application of a peak finding algorithm to locate the 511 keV peaks and may occasionally cause the peak-finding algorithm to fail entirely. Curve 120 shows the background spectrum measured without any with no radioactive source loaded, and is principally due to Lu176 background radiation. Curve 130 shows the Na22 calibration source spectrum 110 minus the background spectrum 120. For reference, dashed line 140 indicates the 511 keV peak. It is readily evident that the difference spectrum 130 exhibits a well-isolated 511 keV peak, for which the peak energy is easily determined by a Gaussian fit or other peak finding algorithm.

With continuing reference to FIG. 1, arrows 150 indicate a 307 keV peak in the Na22 calibration source spectrum 110 and in the background spectrum 120. Arrows 160 similarly indicate a 202 keV peaks in the calibration source spectrum 110 and background spectrum 120. Arrows 170 indicate a 88 keV peak in these spectra.

As can be seen, the Na22 calibration source radiation spectrum 110 is noisy, and the lutetium 307 keV peak is stronger than the 511 keV peak in this spectrum 110. After subtraction, the difference spectrum 130 is cleaner and the 511 keV peak stands out and is easier to detect. Once the energy peak (denoted herein as eMax centroid E) is identified, the saturation look-up table as an exponential function can be calculated and the singles events are saturation corrected.

Subsequently, the events may be divided into two groups, clustering events and pixel energy events. The pixel energy events are used to build energy sum (eSum) histogram, which generates a second level correction. Now the lutetium pixel energy events are no longer used and dropped from the process to free up system memories. The next clustering events are corrected using the eSum correction, and clustered together.

In one aspect, subtraction of the background radiation spectrum 120 from the calibration source radiation spectrum 110 simplifies the 511 keV energy acquisition, removes the dominant 307 keV, and lower extraneous peaks overall. In some implementations, the calibration background subtraction method reduces the energy calibration run time by 50% and improves its robustness because of the spectrum simplification. Thus, the technical functioning of nuclear imaging equipment and of processors in the nuclear imaging equipment is improved by the methods described herein.

Figure 2:
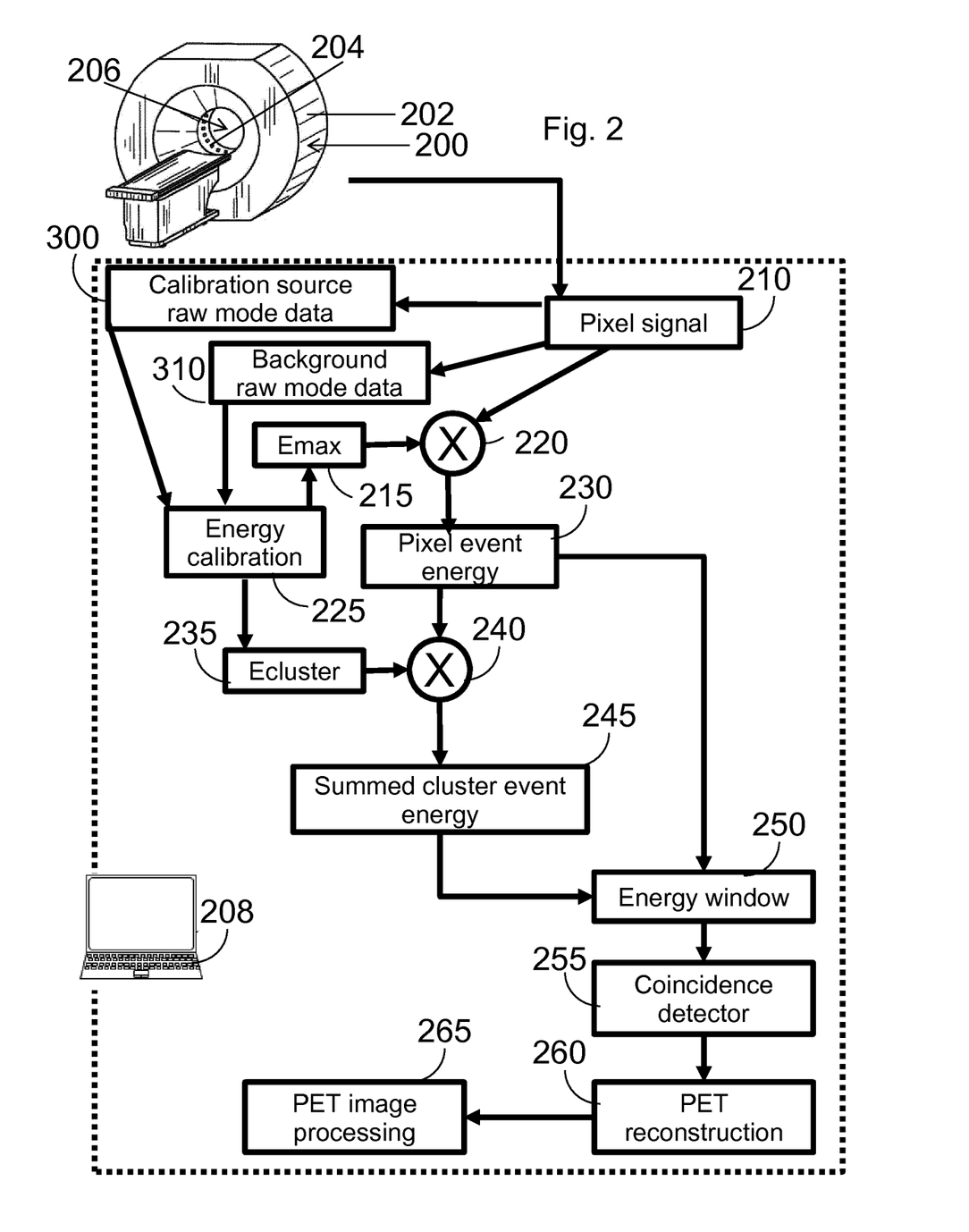
FIG. 2 diagrammatically shows an embodiment of the approaches described herein.

With reference to FIG. 2, a nuclear imaging machine 200, and computer 208 are shown. Nuclear imaging machine 200 is an illustrative positron emission tomography (PET) scanner that includes a housing 202 containing or supporting a radiation detector 204 in the form of a radiation detector ring. The radiation detector ring 204 encircles an examination region 206 into which an imaging subject (e.g., a medical patient injected with a positron-emitting radiopharmaceutical) is loaded for imaging. For the detector calibration including energy calibration, a 511 key-emitting calibration source (e.g. Na22 or Ge68) is loaded into an isocenter of the examination region 206 and the calibration source radiation spectrum 110 (FIG. 1) is acquired. For the disclosed energy calibration approaches, the PET scanner 200 also acquires the background spectrum 120 (FIG. 1) with no radioactive source loaded into the examination region 206. The radiation detector 204 comprises an array of radiation detector pixels, each of generates a pixel signal 210. Energy calibration 225 (an illustrative example of which is described with reference to FIG. 3) provides both Emax 215 and Ecluster 235. In an operation 220, the pixel signal 210 is multiplied by the Emax energy correction factor 215 to produce pixel event energy 230. In an operation 240, the pixel event energy 230 is multiplied by Ecluster 235 to produce a summed cluster event energy 245. The pixel event energy 230 is also sent to energy window 250, which also receives information of the summed cluster event energy 245. Energy-corrected imaging event data are produced by filtering using the energy-selective window 250 to select imaging event data at the known energy of the radiation emission of interest (namely 511 keV in the case of PET imaging). The 511 keV imaging event data from the energy window 250 are processed by a coincidence detector 255 which performs coincidence detection on the 511 keV imaging event data to identify 511 keV event pairs corresponding to electron-positron annihilation events. Each event pair defines a "line of response" or "LOR" as the positron annihilation event producing the 511 keV event pair occurred along the LOR connecting the two 511 keV event detections. Optionally, time-of-flight (TOF) localization (not shown) is performed for each event pair to further localize the positron annihilation along the LOR. This coincidence data from the coincidence detector 255 is reconstructed in PET reconstruction 260 to generate a reconstructed PET image of the imaging subject. The reconstructed PET image may optionally be further processed by PET image processing 265, for example to perform a clinical diagnostic task.

The processing operations 220, 240, 250, 255, 260, 265 are performed during imaging of an imaging subject, i.e. with an imaging subject such as a medical patient loaded into the examination region 206. On the other hand, during detector calibration per-pixel calibration source raw mode data 300 with the calibration source loaded, and background raw mode data 310 with no radioactive source loaded, are input to the energy calibration 225 which is further described with reference to FIG. 3.

Figure 3:
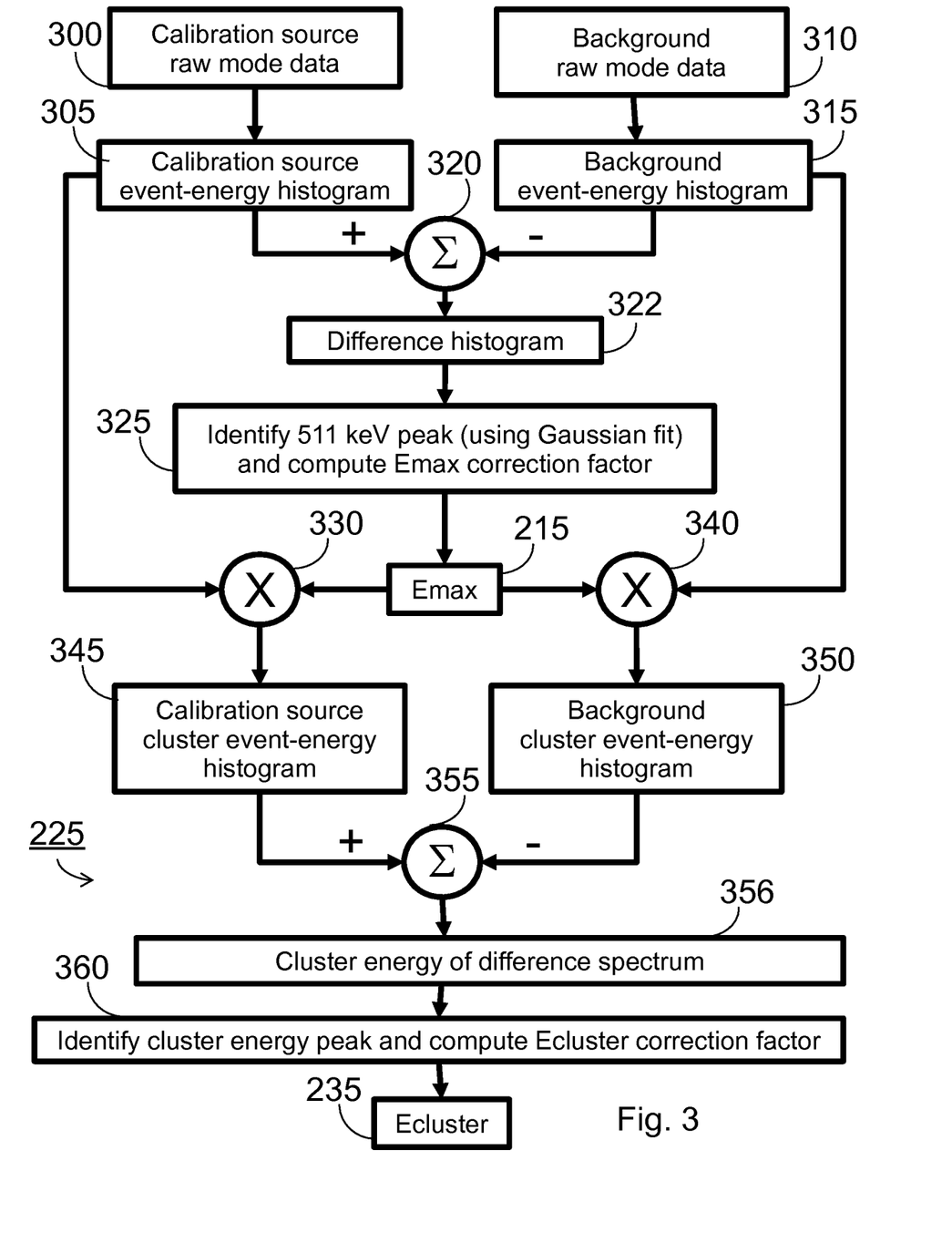
FIG. 3 illustrates an approach related to accounting for cluster detection events.

FIG. 3 illustrates a suitable per-pixel energy calibration method suitably performed by the energy calibration 225. Calibration source raw mode data 300 is used to produce calibration source event-energy spectrum or histogram 305 (corresponding to the exemplary calibration source spectrum 110 of FIG. 1). Background raw mode data 310 is used to produce background event-energy spectrum or histogram 315 (corresponding to the exemplary calibration source spectrum 120 of FIG. 1). In operation 320, a difference is computed between calibration source event-energy histogram 305 and background event-energy histogram 315, so as to produce a difference spectrum 322 (corresponding to the difference spectrum 130 of FIG. 1). The difference spectrum 322 is then used to identify a 511 keV peak (for example, using a Gaussian fit or other peak detection algorithm) and compute the Emax correction factor 215 that is used to correct the imaging data as described with reference to FIG. 2. It should be noted that, since the energy shift in general differs from detector pixel to detector pixel of the radiation detector 204, these operations are preferably repeated for data 300, 310 acquired by each detector pixel to generate the Emax energy correction factor on a per-detector pixel basis. In operation 330, the Emax correction factor 215 is multiplied with the calibration source event-energy histogram 305 to produce the calibration source cluster event-energy histogram 345. Similarly, in operation 340 the Emax correction factor 215 is multiplied with the background event-energy histogram 315 to produce a background cluster event-energy histogram 350. In operation 355, a cluster energy difference spectrum 356 is found between the calibration source cluster event-energy histogram 345 and the background cluster event-energy histogram 350. This is used to identify a cluster energy peak and compute the Ecluster correction factor 235 in operation 360 that is used to correct the imaging data as described with reference to FIG. 2.

In the illustrative embodiment of FIGS. 2 and 3, the Ecluster correction factor 235 is applied after the data are already corrected by the Emax correction factor. In this case the "effective" correction for the cluster data is Emax× Ecluster. Alternatively, the cluster correction factor can be computed from the original calibration source and background histograms 305, 315 without first multiplying by the Emax correction factor, in which case the "effective" correction for the cluster data is the cluster correction factor alone.

In one suitable implementation of the energy calibration, the lutetium data are re-binned into two data files, singles events and energy maximum (eMax, max pixel) histogram. The eMax histogram may then be scaled to the same time period as the Na22 data acquisition. This scaling step allows Lutetium being acquired with fixed time duration, so the actual acquisition can be done during the scanner warm-up period and save the total calibration time.

The reason for having different correction factors Emax, Ecluster is as follows. The output of the Emax calibration is a correction factor that transforms the digital detector signal output by the SiPM of the pixel into an energy value. However, the transformation from digital detector value to energy is not expected to be linear, so the Emax correction factor will be only approximate at lower energies. One way to deal with this is to perform a second calibration with a calibration source in the lower energy range, but this is an extra step that is preferably avoided. In the disclosed approach, the Emax correction factor is applied to both the background and calibration source spectra, and the latter is subtracted from the former before performing the (lower) cluster energy peak calibration.

Figure 4:
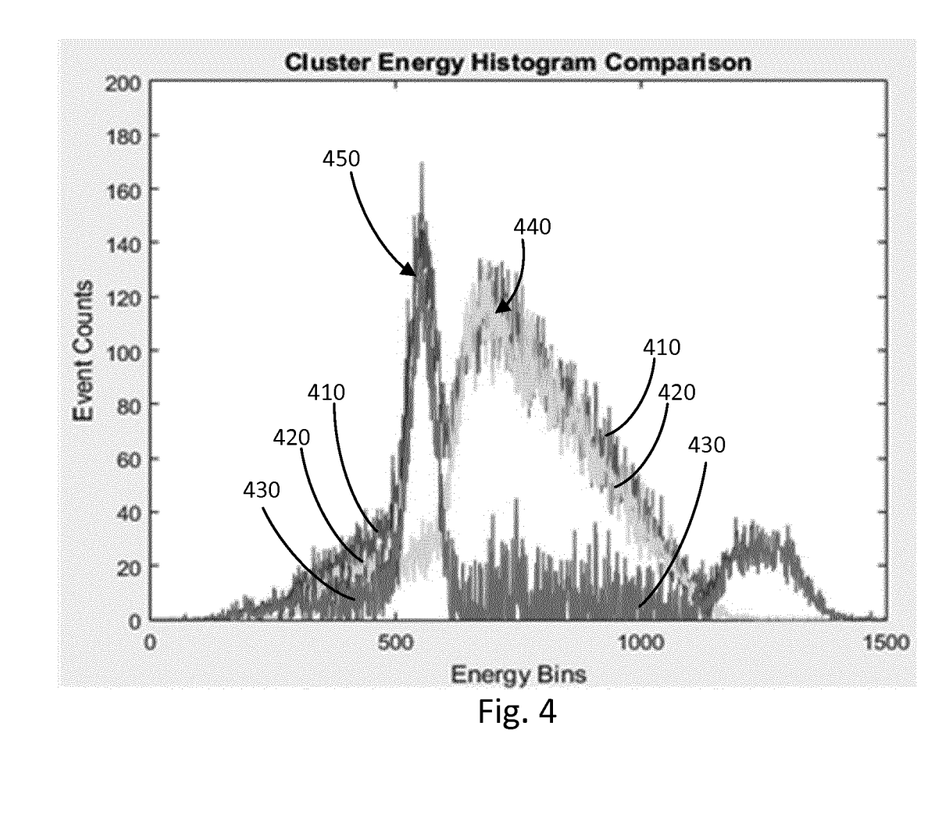
FIG. 4 shows aspects related to clustering by illustrating a clustering energy correction comparison.

FIG. 4 shows acquired radiation spectra related to clustering used in the clustering energy correction. Cluster calibration source spectrum 410 is the spectrum of the Na22 source including the (undesired) lutetium background. Curve 420 shows the background (Lu176) radiation spectrum, and curve 430 shows the cluster energy difference spectrum computed as cluster calibration source spectrum 410 minus the Lu176 spectrum.

When considering cluster events, Lutetium subtraction is again advantageous. Side lobe 440 on the right hand side is much stronger and sometimes too close to the 511 keV peak 450 on left, causing peak detection failure. This side lobe 440 is mainly due to lutetium content. With the lutetium subtraction, it is mostly or completely gone. Finally, the clustered events are used to generate the last clustering histogram. Identifying the peaks produces the energy clustering energy correction.

Figure 5:
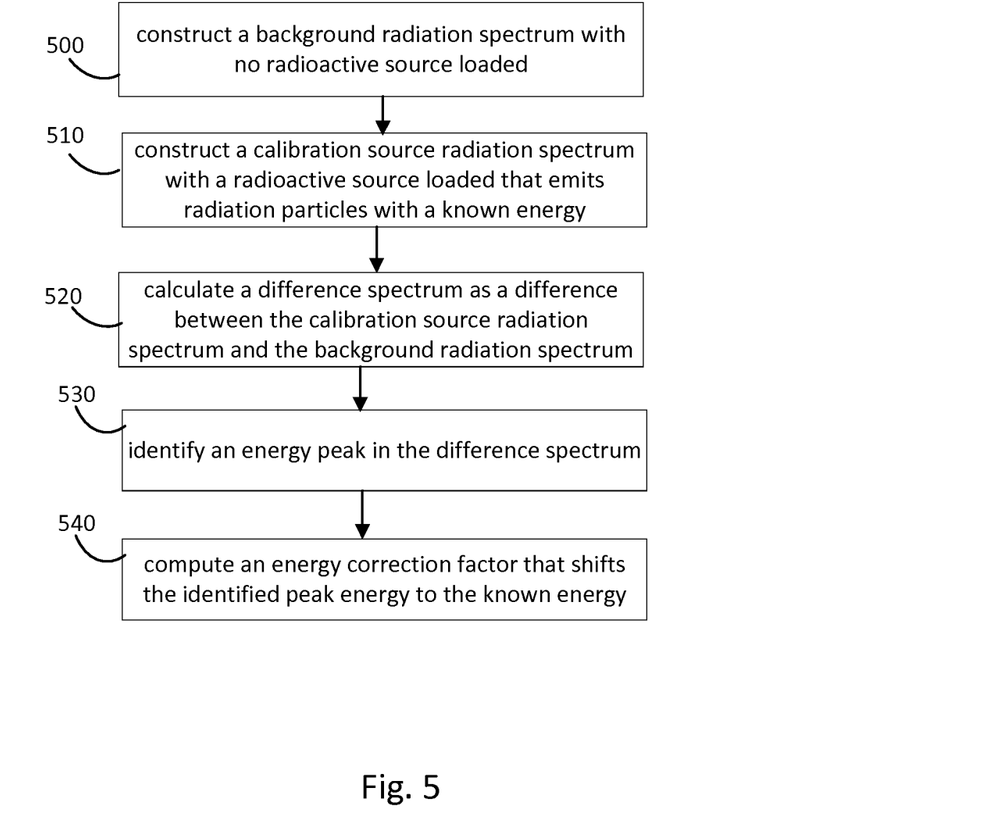
FIG. 5 illustrates an embodiment of a method described herein.

FIG. 5 illustrates an embodiment of a method described herein. With reference thereto, a background radiation spectrum with no radioactive source loaded is constructed in step 500. A calibration source radiation spectrum with a radioactive source loaded that emits radiation particles with a known energy is constructed in step 510. A difference spectrum as a difference between the calibration source radiation spectrum and the background radiation spectrum is calculated in step 520. An energy peak is identified in the difference spectrum based on the calculated difference in step 530. An energy correction factor is computed that shifts the identified peak energy to the known energy in step 540.

It will be further appreciated that the techniques disclosed herein may be embodied by a non-transitory storage medium storing instructions readable and executable by an electronic data processing device (such as the computer 208 or processor(s) of the nuclear imaging machine 200) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A device for performing energy calibration of a nuclear imaging instrument, comprising:
a memory comprising a non-transitory computer-readable storage medium that stores machine executable instructions executable on a processor, wherein, when the machine executable instructions are executed by the processor cause the processor to:
construct a background radiation spectrum from event data acquired by the nuclear imaging instrument with no radioactive source loaded;
construct a calibration source radiation spectrum from event data acquired by the nuclear imaging instrument with a radioactive source loaded that emits radiation particles with a known energy;
calculate a difference spectrum as a difference between the calibration source radiation spectrum and the background radiation spectrum;
identify a peak energy of a peak in the difference spectrum; and
compute an energy correction factor that shifts the identified peak energy to the known energy.

2. The device of claim 1, wherein the nuclear imaging instrument is a positron emission tomography (PET) instrument and the known energy is 511 keV.

3. The device of claim 1, wherein:
the background radiation spectrum comprises a background radiation event count versus energy histogram; and
the calibration source radiation spectrum comprises a calibration source radiation event count versus energy histogram.

4. The device of claim 1, wherein the processor is programmed to identify the peak energy of the peak in the difference spectrum by performing a Gaussian fit to the peak and identifying the peak energy as the mean of the Gaussian fit.

5. The device of claim 1, wherein the at least one electronic processor is further programmed to:
multiply the calibration source radiation spectrum by the energy correction factor to produce a calibration source cluster event-energy spectrum;
multiply the background radiation spectrum by the energy correction factor to produce a background cluster event-energy spectrum;
calculate a cluster energy difference spectrum by subtracting the background cluster event-energy spectrum from the calibration source cluster event-energy spectrum;
identify a cluster peak energy of a lower-energy peak in the cluster energy difference spectrum wherein the identified cluster peak energy is lower than the identified peak energy; and
compute a cluster energy correction factor that shifts the identified cluster peak energy to a known cluster energy corresponding to the known energy.

6. The device of claim 1, wherein the at least one electronic processor is further programmed to:
control the nuclear imaging instrument to acquire imaging event data with an imaging subject loaded;
multiply energy values of the imaging event data by the energy correction factor to generate energy-corrected imaging event data;
filter the energy-corrected imaging event data using an energy-selective window to select imaging event data at the known energy; and
reconstruct the imaging event data at the known energy to generate a reconstructed image of at least a portion of the imaging subject.

7. The device of claim 6, wherein the at least one electronic processor is further programmed to cause a display device to display the reconstructed image.

8. The device of claim 6, wherein the nuclear imaging instrument is a positron emission tomography (PET) instrument and the known energy is 511 keV and the at least one electronic processor is programmed to reconstruct the imaging event data at 511 keV to generate a reconstructed PET image of at least a portion of the imaging subject by operations including performing coincidence detection on the imaging event data at 511 keV to identify 511 keV event pairs corresponding to electron-positron annihilation events.

9. The device of claim 1, wherein the nuclear imaging instrument includes a detector array comprising radiation detector pixels and the at least one electronic processor is programmed to construct the background and calibration source radiation spectra, calculate the difference spectrum, identify the peak energy, and compute the energy correction factor on a per-pixel basis to compute pixel-specific energy correction factors.

10. The device of claim 9, wherein the at least one electronic processor is further programmed to:
control the nuclear imaging instrument to acquire imaging event data with an imaging subject loaded;
multiply energy values of the imaging event data acquired by each radiation detector pixel by its corresponding pixel-specific energy correction factor to generate energy-corrected imaging event data; and reconstruct the energy-corrected imaging event data to generate a reconstructed image of at least a portion of the imaging subject.

11. A positron emission tomography (PET) imaging device comprising:
    a PET imaging detector comprising scintillators optically coupled with photodetectors, the PET imaging detector comprising detector pixels; and
    a memory comprising a non-transitory computer-readable storage medium that stores machine executable instructions executable on a processor, wherein, when the machine executable instructions are executed by the processor cause the processor to, for each detector pixel:
        construct a background radiation spectrum from event data acquired by the detector pixel with no radioactive source loaded;
        construct a calibration source radiation spectrum from event data acquired by the detector pixel with a radioactive source loaded that emits 511 keV radiation;
        calculate a difference spectrum as a difference between the calibration source radiation spectrum and the background radiation spectrum;
        identify a peak energy of a peak in the difference spectrum; and
        compute an energy correction factor that shifts the identified peak energy to 511 keV.

12. The PET imaging device of claim 11 wherein the scintillators comprise lutetium which produces background radiation overlapping the 511 keV peak in the calibration source radiation spectrum.

13. The PET imaging device of claim 11 wherein the scintillators produce background radiation interfering with the 511 keV peak in the calibration source radiation spectrum.

14. The PET imaging device of claim 11, wherein the at least one electronic processor is further programmed to:
    control the PET imaging detector to acquire PET imaging event data from an imaging subject;
    multiply energy values of the PET imaging event data acquired by each detector pixel by the energy correction factor computed for that detector pixel to generate energy-corrected PET imaging event data; and
    reconstruct the energy-corrected PET imaging data to generate a reconstructed image of at least a portion of the imaging subject.

15. The PET imaging device of claim 14, wherein the at least one electronic processor is programmed to reconstruct the energy-corrected PET imaging data to generate the reconstructed image by operations including:
    filtering the energy-corrected PET imaging event data using a 511 keV-selective energy window to select energy-corrected 511 keV PET imaging event data;
    after the filtering, performing coincidence detection on the energy-corrected 511 keV PET imaging event data to generate PET imaging line-of-response data; and
    reconstructing the PET imaging line-of-response data to generate the reconstructed image of at least a portion of the imaging subject.

16. The PET imaging device of claim 15, further comprising:
    a display device configured to display the reconstructed image.

17. The PET imaging device of claim 11, wherein the at least one electronic processor is further programmed to, for each detector pixel:
    repeat the identify and compute operations for a lower energy peak of the difference spectrum to compute a cluster energy correction factor that shifts the identified peak energy for the lower energy peak to a cluster energy value for 511 keV events detected by a plurality of adjacent detector pixels.

18. The PET imaging device of claim 11, wherein the at least one electronic processor is further programmed to, for each detector pixel:
    calculate a cluster difference spectrum as a difference between the calibration source radiation spectrum multiplied by the energy correction factor computed for the detector pixel and the background radiation spectrum multiplied by the energy correction factor computed for the detector pixel;
    identify a cluster peak energy of a lower-energy peak in the cluster difference spectrum; and
    compute a cluster energy correction factor that shifts the identified cluster peak energy to a cluster energy value for 511 keV events detected by a plurality of adjacent detector pixels.

19. A nuclear imaging device comprising:
    a nuclear imaging instrument comprising scintillators optically coupled with photodetectors to define an array of detector pixels; and
    a memory comprising a non-transitory computer-readable storage medium that stores machine executable instructions executable on a processor, wherein, when the machine executable instructions are executed by the processor cause the processor to, for each detector pixel:
        construct a background radiation spectrum from event data acquired by the detector pixel with no radioactive source loaded;
        construct a calibration source radiation spectrum from event data acquired by the detector pixel with a radioactive source loaded that emits radiation at a known energy;
        calculate a difference spectrum as a difference between the calibration source radiation spectrum and the background radiation spectrum;
        identify a peak energy of a peak in the difference spectrum corresponding to the known energy; and
        compute an energy correction factor that shifts the identified peak energy to the known energy.

20. The nuclear imaging device of claim 19, wherein the nuclear imaging instrument is a positron emission tomography (PET) instrument or a single photon emission tomography (SPET) instrument.

* * * * *